United States Patent [19]

Grollier et al.

[11] Patent Number: 4,800,080

[45] Date of Patent: Jan. 24, 1989

[54] CAPILLARY COSMETIC COMPOSITION FOR WASHING DISENTANGLING HAIR CONTAINING A PLANT EXTRACT CONTAINING SAPONINS

[75] Inventors: Jean-Francois Grollier, Paris; Bernard Beauquey, Clichy, both of France

[73] Assignee: Societe Anonyme dite: L'Oreal, Paris, France

[21] Appl. No.: 896,580

[22] Filed: Aug. 18, 1986

Related U.S. Application Data

[63] Continuation of Ser. No. 679,282, Dec. 7, 1984, abandoned, which is a continuation of Ser. No. 402,801, Jul. 28, 1984, abandoned, which is a continuation of Ser. No. 144,452, Apr. 28, 1980, abandoned.

[30] Foreign Application Priority Data

May 15, 1979 [LU] Luxembourg ............................ 81256

[51] Int. Cl.$^4$ .......................... A61K 7/06; A61K 7/09; A61K 35/78
[52] U.S. Cl. .................................... 424/74; 424/195.1; 424/71
[58] Field of Search ............................ 424/74, 71, 195

[56] References Cited

U.S. PATENT DOCUMENTS 3,904,748  9/1975  Eckert et al. ........................ 424/71
3,980,769  9/1976  Ghilardi et al. ...................... 424/71
4,349,532  9/1982  Vanlerberghe et al. .............. 424/71

FOREIGN PATENT DOCUMENTS 1048154  12/1953  France .
1082210  12/1954  France .
1310160  10/1962  France .
1312458  11/1962  France .
1443889   5/1966  France .
2180490  11/1973  France .
58-12975  4/1973  Japan .

OTHER PUBLICATIONS

Goldenberg, *D & CI*, pp. 30 and 138 (Feb. 1976) (in parent Ser. No. 144,452).
Bergwein, *Amer. Perfumes & Cosmetics*, vol. 83, pp. 41–43 (May, 1968).
De Navarre, *The Chem. & Mafr. of Cosmetics*, (2d ed.), vol. 2, pp. 42–45, 290–292 (1962).
*Cosmetic Materials*, pp. 403–404 (1962).

*Primary Examiner*—Albert T. Meyers
*Assistant Examiner*—Freda L. Krosnick
*Attorney, Agent, or Firm*—Cushman, Darby & Cushman

[57] ABSTRACT

A capillary cosmetic composition for washing or disentangling hair comprises in an appropriate cosmetic vehicle at least one plant extract, the active principle of which is at least one saponin and at least one cationic polymer.

2 Claims, No Drawings

CAPILLARY COSMETIC COMPOSITION FOR WASHING DISENTANGLING HAIR CONTAINING A PLANT EXTRACT CONTAINING SAPONINS

This is a continuation of application Ser. No. 679,282, filed Dec. 7, 1984, which was abandoned upon the filing hereof, which application is a continuation of Ser. No. 402,801, filed July 28, 1982, now abandoned which in turn is a continuation of Ser. No. 144,452, filed Apr. 28, 1980, now abandoned.

The present invention relates to a capillary cosmetic composition principally for the washing and/or the disentangling of hair, based on a plant extract containing saponin. The composition also contains at least one cationic polymer.

It has already been proposed to use as capillary compositions, principally for washing and/or rinsing hair, those containing, in addition to a surfactant, at least one cationic polymer. The cationic polymer not only imparts to the hair a shiny appearance and a certain flexibility but it also facilitates disentanglement of the hair.

Such compositions, however, exhibit certain disadvantages which interfere with the aesthetic appearance of the hair. In effect, the combination of a synthetic surfactant with at least one cationic polymer most often causes a rapid re-oiling of the hair, so that it is necessary to wash the hair quite frequently.

It has been observed that this abnormal re-oiling of the hair occurs notwithstanding what type of surfactant is employed.

Moreover, it has also been observed that in certain combinations of these components, a large number of polymers exhibit too significant a substantivity for the hair which prevents good removal with washing. It has further been observed that other polymers impart static electricity to the hair thus making it particularly difficult to achieve a good hair style.

The present invention resides in the surprising discovery that this hair re-oiling effect does not occur or, if it does, only very slightly when the cationic polymers are combined with a natural surfactant and principally with plant extracts containing saponins.

Although with the use of synthetic surface active agents on normal hair a re-oiliness appears from the second or third day after a shampoo, it has been observed that with the use of the combination of components in accordance with the present invention any re-oiliness occurs only on the fifth day after a shampoo which is quite remarkable and surprising.

Besides, it has been noted that hair treated with the aid of the composition according to the present invention is more flexible and more easy to style, it being less electric.

The present invention thus relates to a new industrial product comprising a capillary cosmetic composition for use principally in washing and/or disentangling hair, comprising in a suitable cosmetic vehicle (i) at least 0.5 weight percent, expressed on a dry basis, of at least one plant extract, the active principle of which comprises essentially at leat one saponin, and (ii) at least one cationic polymer.

Saponins are constituted on the one hand by a sapogenin and on the other hand by a mono-saccharide.

The sapogenin can be either steroidic, or triterpenic. Representative plants yielding extracts whose sapogenins have a steroidic structure include, in particular:

(1) those belonging to the Liliaceous family and principally:

(a) the Smilax species (sarsaparilla), for example: *Smilax aspera L, Smilax officinalis, Smilax regilii, Smilax glaberrina, Smilax medica, Smilax aristolochiaefolia, Smilax papyraceae, Smilax febrifuga, Smilax ornata, Smilax saluberina* and *Smilax china;*

(b) the Asparagus species, for example: *Asparagus officinalis L, Asparagus persicus, Asparagus tenufoluis;*

(c) the Yuccas species, for example: *Yucca filifera, Yucca treculeana, Yucca glauca, Yucca filamentosa, Yucca gloriosa* and *Yucca Shottii,* and (d) the Ruscus species, for example: *Ruscus Aculeatus L* (housson);

(b 2) those belonging to the Discoreaceous family, such as the Discoreas species, for example: *Discorea tokoro, Discorea mexicana, Discorea toxicaria* and *Discorea sylvatica;* and (3) those belonging to the Amaryllidaceous family, such as the Agaves species, for example: *Agave sisalana* and *Agave Fourcroydes.*

Representative plants yielding extracts whose sapogenins have a triterpenic structure, include, in particular:

(1) those belonging to the Rosaceous family, for example: *Quillaya Saponaria* (Panama bark);

(2) those belonging to the Hippocastanaceous family, for example: *Aesculus hippocastanum L* (horse-chestnut);

(3) those belonging to the Zygophyllaceous family, for example: *Gaiacum Officinalis L* (*lignum vitae*);

(4) those belonging to the Leguminous family, for example: Glycyrrhiza Glabra L (licorice);

(5) those belonging to the Caryophyllaceous family and principally the Gypsophila species, for example: *Gypsophila paniculata, Gypsophila struthium* and *Saponaria officinalis* (soapwort);

(6) those belonging to the Araliaceous family, for example: *Hedera Helix L* (ivy):

(7) those belonging to the Polygalaceous family, for example: *Polygala Senega;* and (8) those belonging to the Sapindaceous family, for example: *Sapindus Saponaria.*

The extracts of the plants listed above are obtained according to various processes and principally by maceration, digestion, decoction, infusion, lixiviation or expression.

All these extraction methods are well known to the skilled artisan and are described in detail in the book, "L'Officine"-by Dorvault, Edition Vigot 1978, pp. 569-573.

There can also be employed to obtain the plant extracts the process described in French Pat. Nos. 2.126.523, 2,227.876 and 2,241.563 the latter corresponding to U.S. Pat. No. 3,992,315, and, more particularly, the process described in French Pat. No. 1.520.375, which corresponds to U.S. Pat. No. 3,351,582, all incorporated herein by reference.

This latter process comprises treating the plants (roots, bark, leaves, flowers, fruits, etc.), previously ground in the presence of an aliphatic alcohol having 1-3 carbon atoms (methanol, ethanol, isopropanol) at about 65-75%, and concentrating the resulting product under a vacuum until it has a pasty consistency. The extract obtained is then taken up in boiling water, which is then cooled and the insoluble portion is filtered off. The fraction soluble in water can then be concentrated so as to provide liquid or dry extracts or it can optionally be treated again so as to yield extracts which are more pure or which are more enriched in saponins.

The aliphatic alcohol, for certain species of plants, can be replaced by a mixture of water and ethyl acetate or acetone.

All the extracts obtained by these processes are characterized by the fact that they contain saponins, the sapogenins of which have either a steroidic structure or a triterpenic structure.

Generally, the extracts used in accordance with the present invention are mixtures which can contain different saponins present in an amount greater than 10 weight percent relative to the dry matter.

For instance, the following extracts can be employed in the present invention: an ivy extract containing 60 percent saponins, a sarsaparilla extract having 50 percent saponins, a Saponaria extract containing 40-50 percent saponins, a *Polygala Senega* extract having 50 percent saponins, and a horse-chestnut extract with 50-70 percent saponins.

In accordance with another embodiment of the invention, the extracts can be enriched in one or more saponins and can be obtained, preferably, by the purification process described in French Pat. No. 1.520.375 which corresponds to U.S. Pat. No. 3,351,582. This process yields extracts containing more than 90 weight percent of at least one saponin.

Representative saponins which can be used in the present invention include, for instance, those having steroidic-structured sapogenins such as: Asperoside (*Smilax aspera*), Sarsapogenin (*Smilax regilii, Smilax medica* and Yucca species), and Smilagenin (*Smilax ornata*).

Representative saponins that can be used in the present invention having triterpenic-structured sapogenins are: quillayic acid (*Quillaya Saponaria* and *Saponaria Officinalis*), gypsogenin and gypsogenic acid (*Gypsophilia* and *Saponaria Officinalis*), hederagenin (*Hedera Helix* and *Sapindus Saponaria*), oleanolic acid (*Hedera Helix, Panax Ginseng, Gaiac*), Senegenin (*Polygala Senega*), protoescigenin (*Aesculus Hippocastanum*), and glycyrretic acid (*Glycyrriza Glabra*).

The cationic polymers used in the compositions of this invention are polymers of the polyamine, quaternary ammonium or polyamino-amide type wherein the amine or ammonium group is a part of the polymeric chain or is linked thereto.

Representative polymers of this type which can be used in accordanace with the invention include, principally:

(1) vinylpyrrolidone-amino alcohol acrylate or methacrylate (quaternized or not) such as those sold under the tradenames "Gafquat" by GAF Corp., as, for example, "copolymer 845" and "Gafquat 734 or 755", described principally in more detail in French Pat. No. 2.077.143 which corresponds to U.S. Pat. No. 3,910,862;

(2) cellulose ether derivatives having quaternary ammonium groups such as those described in French Pat. No. 1.492.597 which corresponds to U.S. Pat. No. 3,472,840, and principally polymers sold under the tradename "JR" such as "JR 125", "JR 400" and "JR 30M", and under the tradename "LR" such as "LR 400" and "LR 30M" by Union Carbide; and cationic cellulose derivatives such as Experimental Polymer 78.43.29 sold by National Starch;

(3) quaternized guar gum derivatives such as "Jaquar C.13S" sold by Celanese;

(4) cationic polymers selected from (a) polymers of the formula: —A—Z—A—Z— (III) wherein A represents a radical having two amine functions and preferably

and Z represents B or B'; B and B', each independently, represent a bivalent radical which is a straight or branched chain alkylene having up to 7 consecutive carbon atoms in the principal chain, unsubstituted or substituted by hydroxyl groups and also capable of having oxygen, nitrogen or sulfur atoms, 1-3 aromatic or heterocyclic rings; the oxygen, nitrogen and sulfur atoms can be present in the form of an ether or thioether group, a sulfoxide, a sulfone, a sulfonium, an amine, an alkylamine, an alkenylamine, a benzylamine, an amine oxide, a quaternary ammonium, an amide, an imide, an alcohol ester and/or a urethane. These polymers and the process of their preparation are described in French Pat. No. 2.162.025 which corresponds to U.S. Pat. No. 3,917,819;

(b) a polymer of the formula: —A—$Z_1$—A—$Z_1$— (IV) wherein A represents a radical having two amine functions and preferably,

and $Z_1$ represents $B_1$ or $B'_1$ and it represents at least once the symbol $B'_1$; $B_1$ represents a bivalent radical which is a straight or branched chain alkylene or hydroxyalkylene having up to 7 carbon atoms in the principal chain, $B'_1$ is a bivalent radical which is a straight or branched chain alkylene having up to 7 carbon atoms in the principal chain, unsubstituted or substituted by one or more hydroxyl radicals and interrupted by one or more nitrogen atoms. The nitrogen atom is substituted by an alkyl chain having optionally 1-4 atoms and preferably 4 carbon atoms, interrupted optionally by an oxygen atom and having necessarily one or more hydroxyl functions; and (c) quaternary ammonium salts and the oxidation products of polymers of formulas (III) and (IV) indicated above in paragraphs (a) and (b). The polymers of formula (IV) and the process for their preparation are described in French Pat. No. 2.280.361 which corresponds to U.S. Pat. No. 4,013,787;

(5) crosslinked polyamino-amides, optionally alkylated, selected from the group consisting of at least one crosslinked polylmer soluble in water, obtained by crosslinking a polyamino-polyamide (A) prepared by polycondensation of an acid compound with a polyamine. The acid compound is selected from (i) organic dicarboxylic acids, (ii) aliphatic mono- or di-carboxylic ethylenically unsaturated acids, (iii) esters of the aforementioned acids, preferably esters of lower alkanols having 1-6 carbon atoms; and (iv) mixtures of (i), (ii) and (iii).

The polyamine is selected from among the bis primary and mono- or di-secondary polyalkylene-polyamines. 0 to 40 mole percent of this polyamine can be replaced by a bis primary amine, preferably, ethylene diamine or by a bis-secondary amine, preferably piperazine, and 0 to 20 mole percent can be replaced by hexamethylenediamine. The crosslinking is effected by means of a crosslinking agent (B) selected from epihalohydrins, diepoxides, dianhydrides, unsaturated anhydrides, and bis unsaturated derivatives. The crosslinking is characterized by the fact that it is carried out by means of 0.025–0.35 mole of crosslinking agent per amine group of the polyamino-polyamide (A) and generally from 0.025 to about 0.2 mole, and, in particular, from 0.025 to about 0.1 mole of crosslinking agent per amine group of the polyamino-polyamide (A). These polymers and their preparation are described in greater detail in French Pat. No. 2.252.840 which corresponds to U.S. Pat. No. 4,172,887.

This crosslinked polymer is perfectly soluble in water up to 10% without the formation of a gel. The viscosity of a 10% solution in water at 25° C.is greater than 3 centipoises and is usually between 3 and 200 centipoises.

The crosslinked polyamino-amides, optionally alkylated, have no reactive groups, have no alkylating characteristics and are chemically stable.

The polyamino-amides (A), per se, are also useful in the present invention;

(6) water soluble crosslinked polyamino-amides obtained by crosslinking a polyamino-amide (A), described above, by means of a crosslinking agent selected from (I) compounds selected from the group of (1) bis halohydrins, (2) bis azetidinium, (3) bis haloacyls of diamines and (4) alkyl bis halides;

(II) oligomers obtained by reaction of a compound (a) selected from (1) bis halohydrins, (2) bisazetindinium, (3) bis haloacyls of diamines, (4) alkyl bis halides, (5) epihalohydrins, (6) diepoxides and (7) bis unsaturated derivatives, with a compound (b) which is a bifunctional compound reactive vis-a-vis compound (a); and (III) the quaternization product of a compound selected from compounds (a) and oligomers (II) and having one or more tertiary amine groups totally or partially alkylated with an alkylating agent (c) selected, preferably, from the chlorides, bromides, iodides, sulfates, mesylates and tosylates of methyl or ethyl, benzyl chloride or bromide, ethylene oxide, propylene oxide and glycidol, the crosslinking being effected by means of 0.025 to 0.35 mole, particularly, 0.025 to 0.2 mole, and more particularly, 0.025 to 0.1 mole of crosslinking agent per amine group of the polyamino-amide.

These crosslinking agents and these polymers, as well as the process for their preparation, are described in French Pat. No. 2.368.508 which corresponds to U.S. Pat. No. 4,189,468 incorporated herein by reference;

(7) water soluble derivatives of polyamino-amides resulting from the condensation of polyalkylene polyamines with polycarboxylic acids, followed by alkylation using bifunctional agents such as the adipic acid/-dialkylamino hydroxy alkyl/dialkylene triamine copolymers in which the alkyl radical has 1-4 carbon atoms and represents, preferably, methyl, ethyl and propyl, described in French Pat. No. 1.583.363 which corresponds to U.S. Pat. No. 3,632,559.

The compounds providing intersecting results are the adipic acid/dimethylamino hydroxy/propyl diethylenetriamine copolymers sold under the tradename "Cartaretine F, F₄ or F₈" by Sandoz;

(8) polymers obtained by the reaction of a polyalkylene polyamine having two primary amine groups and at least one secondary amine group with a dicarboxylic acid selected from diglycolic acid and saturated aliphatic dicarboxylic acids having 3–8 carbon atoms. The molar ratio between the polyalkylene polyamine and the dicarboxylic acid is between 0.8:1 and 1.4:1; the resulting polyamide being caused to react with epichlorohydrin in a molar ratio of epichlorohydrin relative to the secondary amine group of the polyamide between 0.5:1 and 1.8:1, as set forth in U.S. Pat. Nos. 3,277,615 and 2,961,347, both incorporated herein by reference.

Particularly interesting polymers are those sold under the tradename "Hercosett 57" by Hercules, having a viscosity at 25° C. of 30 centipoises in a 10% aqueous solution; those sold under the tradename "PD 170" or "Delsett 101" by Hercules in the case of an adipic acid-/epoxypropyl diethylene triamine copolymer;

(9) water soluble cyclopolymers having a molecular weight of 20,000 to 3,000,000, such as homopolymers having as the principal chain component, units having formula (II) or formula (II'):

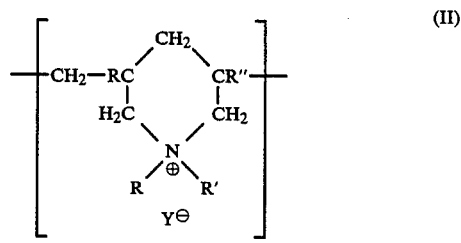

or

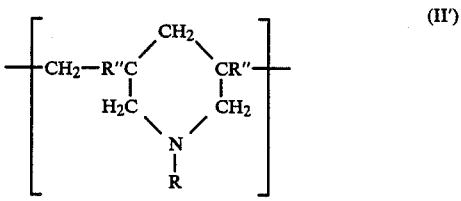

wherein R″ represents hydrogen or methyl, R and R′ each independently represent alkyl having 1–22 carbon atoms, hydroxy alkyl wherein the alkyl moiety has preferably 1–5 carbon atoms and lower amidoalkyl, and where R and R′ can represent together with the nitrogen atom to which they are attached a heterocycle group such as piperidinyl or morpholinyl, as well as copolymers having units of formula II or formula II′ and, preferably, acrylamide or diacetone acrylamide derivatives, and $Y^\ominus$ is an anion such as bromide, chloride, acetate, borate, citrate, tartrate, bisulfate, bisulfite, sulfate or phosphate.

Among the quaternary ammonium polymers of the type defined above, those which are more particularly preferred, are homopolymers of dimethyl diallyl ammonium chloride sold under the tradename "Merquat 100" having a molecular weight lower than 100,000 and the copolymer of dimethyl diallyl ammonium chloride and acrylamide having a molecular weight greater than 500,000 and sold under the tradename "Merquat 550" by Merck.

These polymers are described in French Pat. No. 2.080.759 and its certificate of addition No. 2.190.406 which correspond to U.S. Pat. Nos. 3,912,808; 3,986,825 and 4,027,008;

(10) quaternary polyammoniums of the formula

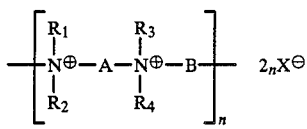

wherein $R_1$, $R_2$, $R_3$ and $R_4$, each independently, represent aliphatic, alicyclic or arylaliphatic radicals containing at most 20 carbon atoms, or lower hydroxy aliphatic radicals, or even $R_1$, $R_2$, $R_3$ and $R_4$ together or separately, can constitute with the nitrogen atoms to which they are attached, heterocycles containing, optionally, a second heteroatom other than nitrogen, or even $R_1$, $R_2$, $R_3$ and $R_4$ can represent

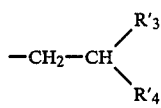

wherein $R'_3$ represents hydrogen or lower lower alkyl and $R'_4$ represents

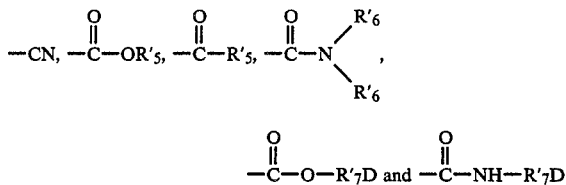

wherein $R'_5$ represents lower alkyl, $R'_6$ represents hydrogen or lower alkyl, $R'_7$ represents alkylene and D represents a quaternary ammonium group. A and B can represent polymethylene groups containing from 2 to 20 carbon atoms and can be linear or branched, saturated or unsaturated, containing, interposed in the principal chain, one or more aromatic rings such as

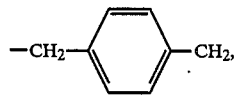

or one or more of such groups as —CH$_2$—Y—CH$_2$ wherein Y represents, O, S, SO, SO$_2$,

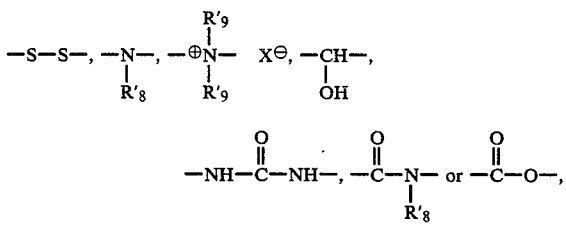

wherein $X^{\ominus}$ represents an anion derived from a mineral or organic acid, $R'_8$ represents hydrogen or lower alkyl and $R'_9$ represents lower alkyl. A and $R_1$ and $R_3$ can also form with the two nitrogen atoms to which they are attached a piperazine ring; moreover, if A represents an alkylene or hydroxy alkylene radical, linear or branched, saturated or unsaturated, B can also represent —(CH$_2$)$_n$—CO—D—OC—(CH$_2$)$_n$—, wherein D represents (a) a glycol residue of the formula —O—Z—O— wherein Z represents a linear or branched hydrocarbon radical, or a group having one of the following formulas:

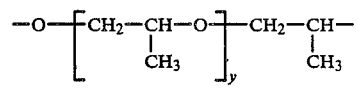

wherein x and y representing a whole number from 1 to 4 designates a definite and unique degree of polymerization, or any number from 1 to 4 represents an average degree of polymerization, (b) the residue of a bissecondary diamine such as a derivative of the formula $$-N\underset{\underbrace{\phantom{XXXX}}}{\overset{\overbrace{\phantom{XXXX}}}{\phantom{XX}}}N-,$$

(c) the residue of a bis-primary diamine of the formula, —NH—Y—NH— where Y represents a linear or branched hydrocarbon, or the bivalent radical, —CH$_2$—CH$_2$—S—S—CH$_2$—CH$_2$— or (d) a ureylene group of the formula, —NH—CO—NH—; $X^{\ominus}$ is an anion such as chloride or bromide, and n is such that the molecular mass is between 1,000 and 100,000.

Polymers of this type are described, in particular, in French Pat. Nos. 2.320.330 and 2.270.846 which correspond, respectively, to U.S. Pat. Nos. 4,075,136 and 4,217,914, in French application Nos. 76.20261 and 2.336.434, and in U.S. Pat. Nos. 2,273,780; 2,375,853; 2,388,614; 2,454,547; 3,206,462; 2,261,002; and 2,271,378, all incorporated herein by reference.

Other polymers of this type are described in U.S. Pat. Nos. 3,874,870; 4,001,432; 3,929,990; 3,966,904; 4,005,193; 4,025,617, 4,025,627; 4,025,653; 4,026,945 and 4,027,020, all incorporated herein by reference.

Other useful cationic polymers are the polyalkylene imines and, in particular, the polyethylene imines, the polymers containing in the chain vinylpyridine or vinylpyridinium units, the condensates of polyamines and epichlorohydrin and quaternary polyureylenes.

The composition of the present invention is an aqueous composition containing the saponin-based plant extract in an amount between 0.5 and 20 weight percent, expressed on a dry basis, and the cationic polymer in an amount between 0.05 and 10 weight percent and preferably between 0.2 and 3 weight percent, relative to the total weight of the composition.

The capillary compositions of the present invention have a pH between 2 and 9 and, preferably, between 4 and 8.

They can contain, in addition to water, any cosmetically acceptable solvent selected from monoalcohols, including, for instance, alkanols having between 1-8 carbon atoms such as ethanol, isopropanol, benzyl alcohol and phenylethyl alcohol; polyalcohols including, for instance, alkylene glycols such as ethylene glycol and propylene glycol; glycol ethers including, for instance, the mono-, di- and tri-ethylene glycolmonoalkyl ethers such as ethylene glycolmonomethyl ether, ethylene glycolmonoethyl ether and diethyleneglycolmonoethyl ether, used alone or in admixture.

These solvents are present in amounts lower than or equal to 70 weight percent relative to the total weight of the composition.

The composition of the present invention can be provided in the form of a solution, a dispersion or a gel.

Moreover, the composition of this invention more particularly comprises a shampoo, rinse lotion for application to the hair, before or after a shampoo, a hair setting lotion, a brushing lotion and a hair treating composition.

When the composition is provided in the form of a shampoo, it can also contain an anionic, nonionic, cationic or amphoteric surfactant or a mixture thereof.

Representative anionic surfactants include, for instance, the following compounds as well as mixtures thereof: the alkaline salts, the ammonium salts, the amine salts or the amino alcohol salts of the following compounds:

(1) alkyl sulfates, alkylether sulfates, alkylamide sulfates and ethersulfates, alkylarylpolyether sulfates and monoglyceride sulfates, (2) alkylsulfonates, alkylamide sulfonates, alkylarylsulfonates and α-olefin sulfonates.

(3) alkylsulfosuccinates, alkylethersulfosuccinates, alkylamidesulfosuccinates and alkylsulfosuccinamates, (4) alkylsulfoacetates and alkylpolyglycerol carboxylates, (5) alkylphosphates and alkyletherphosphates, (6) alkylsarcosinates, alkylpolypeptidates, alkylamidopolypeptidates, alkylisethionates and alkyltaurates, wherein the alkyl radical of all the compounds listed in (1)–(6) above is a linear chain having from 12–18 carbon atoms; and (7) fatty acids such as oleic acid, ricinoleic acid, palmitic acid, stearic acid, copra oil acids or hydrogenated copra oil acid, carboxylic acids of polyglycol ethers having the formula: $Alk-(OCH_2-CH_2)_n-OCH_2-CO_2H$ wherein Alk corresponds to a linear chain having 12–18 carbon atoms and wherein n is a whole number between 5 and 15.

Representative nonionic surfactants that can optionally be employed are those described in French Pat. Nos. 2.091.516 which corresponds to U.S. Pat. No. 3,821,372; 3,928,224; 3,966,398 and 4,087,466, 1.477.048 which corresponds to U.S. Pat. No. 3,578,719 and 2.328.763.

Other nonionic surfactants of this type are alcohols, alkylphenols, polyethoxylated or polyglycerolated fatty acids having a linear fatty chain containing 8 to 18 carbon atoms and most often containing 2 to 30 moles of ethylene oxide. Also usefully employed are copolymers of ethylene and propylene oxides, condensates of ethylene and propylene oxides on fatty alcohols, polyethoxylated fatty amides, polyethoxylated fatty amines, ethanolamides, fatty acid esters of glycol, fatty acid esters of sorbitol and the fatty acid esters of sucrose.

Representative cationic surfactants which can be used include, particularly, salts of fatty amines such as alkylamine acetates, quaternary ammonium salts such as alkyl dimethylbenzyl ammonium chloride or bromide, alkyltrimethyl ammonium chloride or bromide, alkyldimethylhydroxyethyl ammonium chloride or bromide, dimethyldistearyl ammonium chloride or bromide, alkylamido ethyltrimethyl ammonium methosulfate, alkylpyridinium salts and imidazoline derivatives. The alkyl radicals in these compounds have, preferably, between 1 and 22 carbon atoms. Also usefully employed are compounds having a cationic character such as amine oxides such as, for instance, alkyldimethylamine oxide or alkylaminoethyl dimethylamine oxide.

Representative amphoteric surfactants that can be employed include, more particularly, alkylamino mono- and di-propionates, betaines such as N-alkyl betaines, N-alkylsulfobetaines and N-alkylamido betaines, cycloimidiniums such as alkylimidazolines, and asparagine derivatives. The alkyl group in these surfactants represents preferably one having from 1 to 22 carbon atoms.

In these shampoo compositions, the amount of surfactant, other than the plant extract, is generally lower than or equal to 50 weight percent, and preferably between 2 and 20 weight percent.

Another preferred embodiment of the invention is the use of a hair rinse lotion to be applied principally before or after a shampoo.

This lotion can be an aqueous or hydroalcoholic solution, an emulsion, a thickened lotion or a gel.

The composition of the present invention can also be provided in the form of a hair styling lotion or a forming lotion also called a brushing lotion, and a non-rinse hair lotion for reinforcing a hair set.

It goes without saying that the composition of the present invention can also contain any other component conventionally employed in cosmetic compositions for the hair such as perfumes, dyes for coloring the composition itself, preservatives, antioxidants, sequesterants, thickening agents, softening agents, synergists, foam stabilizers, sunscreen agents, and peptizing agents, depending, of course, on the particular or specific use contemplated for the composition.

In order to better understand the invention, the following non-limiting examples of cosmetic compositions are given.

EXAMPLES OF COMPOSITIONS

| Example 1 - Hair rinse | |
|---|---|
| Dry extract of ivy | 4 g |
| Cationic polymer in accordance with Example 1a of French Patent No. 2.252.840, the U.S. counterpart of which is Example 1a of U.S. Pat. No. 4,172,887, said cationic polymer being the polycondensate of adipic acid and diethylene triamine crosslinked with epichlorohydrin | 1 g (a.m.-active material) |
| 5-bromo-5-nitro-1,2-dioxane | 0.03 g |
| Triethanolamine, sufficient amount for pH 8 | |
| Water, sufficient amount for | 100 g |
| Example 2 - Non-rinse hair lotion | |
| Dry extract of ivy | 2 g |
| Cationic polymer in accordance with Example 2 of French Patent 2.280.361 | 0.5 g (a.m.) |
| 5-bromo-5-nitro-1,3-dioxane | 0.03 g |
| Citric acid, sufficient amount for pH 8 | |
| Water, sufficient amount for | 100 g |
| Example 3 - Shampoo composition | |
| Dry extract of ivy | 8 g |
| Cationic polymer, "Cartaretine F4" | 0.33 g (a.m.) |
| 5-bromo-5-nitro-1,3-dioxane | 0.03 g |
| Citric acid, sufficient amount for pH 5 | |
| Water, sufficient amount for | 100 g |
| Example 4 - Hair rinse | |
| Dry extract of sarsaparilla | 2.5 g |
| Cationic polymer: polymer of hydroxyethyl-cellulose and epichlorohydrin quaternized with trimethylamine and sold under the tradename "JR 400" | 0.5 g (a.m.) |
| 5-bromo-5-nitro-1,3-dioxane | 0.03 g |

-continued

| | |
|---|---|
| Citric acid, sufficient amount for pH 4 | |
| Water, sufficient amount for | 100 g |
| Example 5 - Shampoo composition | |
| Dry extract of sarsaparilla | 10 g |
| Cationic polymer in accordance with Example 1 of French Patent No. 2.162.025 | 1 g (a.m.) |
| Sodium orthophenylphenate | 0.2 g |
| Citric acid, sufficient amount for pH 7.5 | |
| Water, sufficient amount for | 100 g |
| Example 6 - Shampoo composition | |
| Dry extract of sarsaparilla | 7 g |
| Cationic polymer: quaternary polyvinylpyrrolidone copolymer having a molecular weight of 1,000,000 sold under the tradename "Gafquat" | 1.5 g (a.m.) |
| $C_{12-18}$ alkyl dimethylcarboxymethyl ammonium hydroxide sold under the tradename "Dehyton AB.30" | 3 g (a.m.) |
| Sodium orthophenylphenate | 0.3 g |
| Citric acid, sufficient amount for pH 4 | |
| Water, sufficient amount for | 100 g |
| Example 7 - Shampoo composition | |
| Dry extract of Saponaria | 5 g |
| Cationic polymer: cationic polymer of hydroxyethyl cellulose sold under the commercial designation of "Experimental Polymer 78.43.29" | 0.1 g (a.m.) |
| Ethyl cellosolve | 3 g |
| 5-bromo-5-nitro-1,3-dioxane | 0.03 g |
| Triethanolamine, sufficient amount for pH 5 | |
| Water, sufficient amount for | 100 g |
| Example 8 | |
| Dry extract of Saponaria | 1 g |
| Cationic polymer in accordance with French Patent 2.280.361, the U.S. counterpart of which is Example 2 of U.S. Pat. No. 4,013,787, said cationic polymer being the polycondensate of N,N'—bis (2,3-epoxypropyl) piperazine and piperazine | 0.3 g (a.m.) |
| Compound of the formula, | 3.2 g (a.m.) |

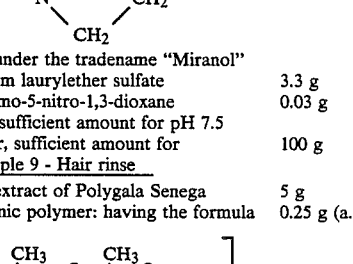

| | |
|---|---|
| sold under the tradename "Miranol" | |
| Sodium laurylether sulfate | 3.3 g |
| 5-bromo-5-nitro-1,3-dioxane | 0.03 g |
| HCl, sufficient amount for pH 7.5 | |
| Water, sufficient amount for | 100 g |
| Example 9 - Hair rinse | |
| Dry extract of Polygala Senega | 5 g |
| Cationic polymer: having the formula | 0.25 g (a.m.) |

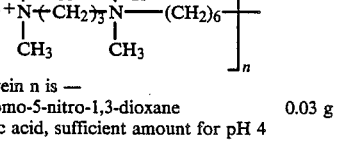

| | |
|---|---|
| wherein n is — | |
| 5-bromo-5-nitro-1,3-dioxane | 0.03 g |
| Citric acid, sufficient amount for pH 4 | |
| Water, sufficient amount for | 100 g |
| Example 10 - Shampoo composition | |
| Dry extract of Polygala Senega | 6 g |
| Cationic polymer: polymer of hydroxyethyl-cellulose and epichlorohydrin quaternized with trimethyl amine and sold under the tradename "JR 400" | 0.1 g (a.m.) |
| Di-sodium salt of ricinoleamido | 2 g (a.m.) |
| monoethanolamine sulfosuccinate sold under the trade name of "Rewoderm S.1333" | |
| Miranol C2M (described in Ex. 18) | 2 g (a.m.) |
| Sodium orthophenylphenate | 0.2 g |
| Triethanolamine, sufficient for pH 7.5 | |
| Water, sufficient for | 100 g |
| Example 11 - Shampoo Composition | |
| Dry extract of horse-chestnut | 5 g |
| Cationic polymer, vinylpyrrolidone quaternary copolymer having a molecular weight of 100,000 sold under the tradename "Gafquat 755" | 0.2 g (a.m.) |
| Mixed salt of sodium and triethanolamine of the lipoamino acids obtained by the combination of lauric acid with the aminated acids resulting from the total hydrolysis of collagen, sold under the tradename "Lipoproteol LCO" | 4 g (a.m.) |
| 5-bromo-5-nitro-1,3-dioxane | 0.03 g |
| Triethanolamine, sufficient amount for pH 7 | |
| Water, sufficient amount for | 100 g |
| Example 12 - Hair rinse | |
| α-escine (pure saponin extract of horse-chestnut) | 0.5 g |
| Cationic polymer: vinylpyrrolidone/ dimethylamino ethyl methacrylate copolymr, sold under the tradename "Gafquat 845" | 0.5 g (a.m.) |
| 5-bromo-5-nitro-1,3-dioxane | 0.03 g |
| Water, sufficient amount for | 100 g |
| The pH of this composition is 8. | |
| Example 13 - Shampoo composition | |
| Dry extract of sarsaparilla | 2 g |
| Saponaria extract | 2 g |
| Cationic polymer: quaternary polyvinylpyrrolidone copolymer having a molecular weight of 1,000,000, sold under the tradename "Gafquat 755" | 0.5 g (a.m.) |
| Potassium salt of the condensate of coconut oil and collagen polypeptides, sold under the tradename "Lamepon S" | 6 g (a.m.) |
| 5-bromo-5-nitro-1,3-dioxane | 0.03 g |
| Triethanolamine, sufficient amount for pH 6 | |
| Water, sufficient amount for | 100 g |
| Example 14 - Non-rinse hair lotion | |
| Dry extract of sarsaparilla | 1 g |
| Dry extract of Saponaria | 0.2 g |
| Cationic polymer: quaternary polyvinylpyrrolidone copolymer having a molecular weight of 100,000, sold under the name of "Gafquat 734" | 0.5 g (a.m.) |
| Ethyl alcohol | 25 g |
| Water, sufficient amount for | 100 g |
| Example 15 - Shampoo composition | |
| Dry extract of Polygala Senega | 4 g |
| Cationic polymer: "JR 400" - See Ex. 10 | 0.05 g (a.m.) |
| 5-bromo-5nitro-1,3 dioxane | 0.03 g |
| Triethanolamine, sufficient amount for pH 5 | |
| Water, sufficient amount for | 100 g |
| Example 16 - Shampoo composition | |
| Dry extract of sarsaparilla | 4 g |
| Cationic polymer: cationic cellulose sold under the tradename "LR 400" | 0.2 g (a.m.) |
| Alkylglucoside of the formula | 3 g (a.m.) |

-continued

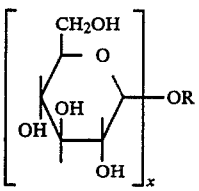

wherein x = 1–5, R = $C_8$ and $C_{20}$ alkyl, sold under the tradename "Triton CG 110"

| | |
|---|---|
| 5-bromo-5-nitro-1,3-dioxane | 0.03 g |
| Triethanolamine, sufficient amount for pH 4.5 | |
| Water, sufficient amount for | 100 g |
| Example 17 - Shampoo composition | |
| Dry extract of quillaja bark | 10 g |
| Cationic polymer: "JR 400" - See Ex. 4 | 0.2 g (a.m.) |
| 5-bromo-5-nitro-1,3-dioxane | 0.03 g |
| Citric acid, sufficient amount for pH 5 | |
| Water, sufficient amount for | 100 g |

What is claimed is:

1. A capillary cosmetic composition for use in washing or disentangling greasy hair whereby rapid re-oiling of the hair either does not occur or occurs only very slightly, said composition comprising in an appropriate cosmetic vehicle (i) between 0.5 and 20 weight percent of a dry saponaria extract containing 40–50 percent saponins and (ii) between 0.05 to 3 weight percent, based on the total weight of said composition, of a cationic polymer, said polymer being a polymer of hydroxyethyl cellulose and epichlorohydrin quaternized with trimethylamine, said composition having a pH between 4 and 8.

2. A method for washing and disentangling greasy hair comprising applying thereto, in an amount sufficient to impregnate the hair, the composition of claim 1.